United States Patent [19]
Krochta

[11] Patent Number: 4,885,387
[45] Date of Patent: Dec. 5, 1989

[54] PRODUCTION OF HIGH YIELDS OF GLYCOLIC AND OXALIC ACIDS FROM POLYSACCHARIDE-CONTAINING MATERIALS

[75] Inventor: John M. Krochta, El Cerrito, Calif.

[73] Assignee: The United States of America as represented by the Secretary of Agriculture, Washington, D.C.

[21] Appl. No.: 155,442

[22] Filed: Feb. 12, 1988

[51] Int. Cl.⁴ .................. C07C 51/295; C07C 51/31; C07C 55/06; C07C 59/06
[52] U.S. Cl. .................................. 562/515; 562/537; 562/539; 252/1
[58] Field of Search ...................... 562/515; 252/1, 398

[56] References Cited
U.S. PATENT DOCUMENTS

| 584,707 | 6/1897 | Roosen | 562/515 |
| 1,001,937 | 8/1911 | Ellis | 562/515 |
| 1,695,742 | 12/1928 | Rawling | 562/513 |
| 1,958,439 | 5/1934 | McKee | 562/513 |
| 1,972,059 | 8/1934 | Bannister | 562/515 |
| 2,024,565 | 12/1935 | Braun | 562/515 |
| 2,750,414 | 6/1956 | Chesley et al. | 562/515 |

FOREIGN PATENT DOCUMENTS

| 1078561 | 11/1955 | Fed. Rep. of Germany | 562/515 |
| 2767 | of 1856 | United Kingdom | 562/515 |

OTHER PUBLICATIONS

J. N. BeMiller, "Alkaline Degradation of Starch," in: Starch: Chemistry and Technology, Eds., R. L. Whistler, E. F. Paschall, J. N. BeMiller, and H. J. Roberts, Academic Press, New York, 1965, vol. I, Chapter XXI.

Primary Examiner—Howard J. Locker
Assistant Examiner—John M. Covert
Attorney, Agent, or Firm—M. Howard Silverstein; John D. Fado; Margaret A. Connor

[57] ABSTRACT

High yields of glycolic and oxalic acids, as well as good yields of lactic, formic, and acetic acids are produced from polysaccharide-containing materials by reacting the materials in a concentrated alkaline solution at elevated temperatures.

12 Claims, 4 Drawing Sheets

YIELDS BASED ON STARTING CELLULOSE

FIG. 1

YIELDS BASED ON STARTING ALKALI

PRODUCTION OF HIGH YIELDS OF GLYCOLIC AND OXALIC ACIDS FROM POLYSACCHARIDE-CONTAINING MATERIALS

BACKGROUND OF THE INVENTION

1. Field of the Invention

The present invention relates to the production of organic acids and salts thereof from polysaccharides, and more particularly to a method of producing high yields of glycolic and oxalic acids by treatment of polysaccharide-containing materials with a concentrated alkaline solution.

2. Description of the Art

Glycolic acid ($HOCH_2COOH$) has several important commercial uses including textile and leather processing; metal cleaning and plating; dairy and food processing sanitation; water well cleaning; masonry cleaning; and production of detergents, adhesives, coatings, and biodegradable polymers. Presently, glycolic acid is produced commercially as an intermediate in one of the processes used for the manufacture of ethylene glycol. This process involves the production of methanol and formaldehyde as intermediates before glycolic acid. The conversion of formaldehyde to glycolic acid requires reaction with carbon monoxide, water, and an acid catalyst at very high pressures, and thus, is very costly. An alternative to the present multi-step method, and in particular, a method wherein high yields of glycolic acid could be readily obtained from polysaccharide material, for example, excess or waste agricultural materials such as starch, corn cobs, cotton waste, and straw residue, would be of great use.

Oxalic acid [$(COOH)_2$] is used commercially for many purposes, for example, as an analytical reagent, in textile and leather processing, in metal cleaning, and as an intermediate for many chemical compounds. Presently, oxalic acid is obtained commercially by passing carbon monoxide into concentrated sodium hydroxide or by heating sodium formate in the presence of sodium hydroxide or sodium carbonate. As with glycolic acid, a method to obtain high yields of oxalic acid from inexpensive polysaccharide sources would be of great value.

Production of organic acids from the reaction of alkali with cellulosic materials is known. Bannister (U.S. Pat. No. 1,972,059) reported the production of primarily acetic, oxalic, formic, and succinic acids, but no glycolic or lactic acids, by alkaline fusion of cellulosic materials in a closed vessel under pressure. A critical feature of the Bannister method is that the cellulosic material, e.g., corn cobs, is fused with caustic soda and small amounts of water (water-to-alkali ratios of 0.2 to 0.6) under pressures of 50 or 75 pounds per square inch (psi). Bannister found that 50 or 75 psi gave results as good as much higher pressures. The reason for the low pressures was the small amount of water Bannister used relative to caustic and cellulosic material.

Chesley et al. (U.S. Pat. No. 2,750,414) reported the production of saturated monocarboxylic acids having 1-3 carbon atoms, principally formic, lactic, acetic, and glycolic acids, by the reaction of celluosic materials in dilute aqueous alkaline solutions at elevated temperatures in a closed system. While a water-to-alkali ratio of 3.5 was used by Chesley et al. (Table 2, run 2), most of the reactions were carried out at water-to-alkali ratios of about 15 and above. In the Chesley et al. process, the formation of oxalic acid does not occur to any substantial extent. A feature of the Chesley et al. method that distinguished it from Bannister is that the celluosic materials had to be reacted with alkali and water in the liquid phase. Thus, although the alkali-to-cellulosic material ratio was approximately the same as Bannister, the water-to-alkali ratio was approximately one to two orders of magnitude larger, and the water-to-cellulosic ratio was much larger. The reaction mixture was a very liquid, free-flowing slurry of cellulosic material in dilute aqueous alkaline solution, compared to Bannister's non-liquid, non-free-flowing, dry-like reaction mass. Given the temperatures studied by Chesley et al. and the larger amount of water used in their closed vessel system, the autogenously developed pressures (about 560–1250 psi) are much greater than Bannister.

SUMMARY OF THE INVENTION

The invention provides a novel method to produce unexpectedly high yields of glycolic and oxalic acids from polysaccharide-containing materials, as well as good yields of lactic, formic, and acetic acids. In the method of the invention, a polysaccharide-containing material is reacted with a concentrated alkaline solution at elevated temperatures.

Surprisingly, by reacting the polysaccharide-containing materials at water-to-alkali ratios intermediate to Bannister and Chesley et al., uniquely high yields of both glycolic and oxalic acids, as well as good yields of lactic, formic, and acetic acids, are obtained. This striking change in both the types and yields of organic acids obtained was unexpected in view of the work of prior investigators. These results contrast with Bannister where large yields of oxalic and acetic acids but no glycolic or lactic acids were obtained, and contrast with Chesley et al. where the formation of oxalic acid does not occur to any substantial extent.

Also in the instant invention, lactic acid yields comparable to Chesley et al. are obtained in addition to the high yields of glycolic and oxalic acids. Another unique feature of the invention is that starch and starch-containing materials may be used as the starting polysaccharide.

In accordance with this discovery it is an object of the invention to provide means to produce high yields of glycolic and oxalic acids and their salts from polysaccharide-containing materials.

A further object of the invention is the production of good yields of lactic, formic, and acetic acids and their salts from polysaccharide-containing materials.

Another object of the invention is the provision of a method to obtain useful organic acids in good yields from starch and other agricultural feedstocks such as cellulose, sawdust, and corn cobs.

Other advantages of the invention will become readily apparent from the ensuing description.

DETAILED DESCRIPTION OF THE INVENTION

The method of the invention requires that the polysaccharide-containing materials be reacted with a concentrated alkaline solution at elevated temperatures. Surprisingly, I have found that by reacting the polysaccharide-containing material with a concentrated alkaline solution wherein the water-to-alkali ratio is in the range of 0.8 to 3, uniquely high yields of oxalic and glycolic acids are obtained. It was unexpected that the thermochemical degradation reaction pathways of polysaccharides which lead to the production of glycolic and oxalic acids would be favored by this select range of water-to-alkali ratios. Such a phenomenon of preferentially high increases in the yields of both these acids had not been observed previously.

The term "water-to-alkali ratio" is used herein to describe the relative amount in parts by weight of water and parts by weight of alkali (based on NaOH) used. Where another alkali is used, an amount of alkali equivalent to ratios based on NaOH is used.

To achieve the concentrated alkaline solutions necessary to obtain the high yields of glycolic and oxalic acids contemplated by the invention, the alkali compounds used must have a high solubility in water. Exemplary of such compounds are the hydroxides and carbonates of sodium and potassium.

Because of the highly concentrated nature of the alkaline solutions used in the invention, the autogenously produced reaction pressures experienced range between about 100–600 psi.

Figure 1:
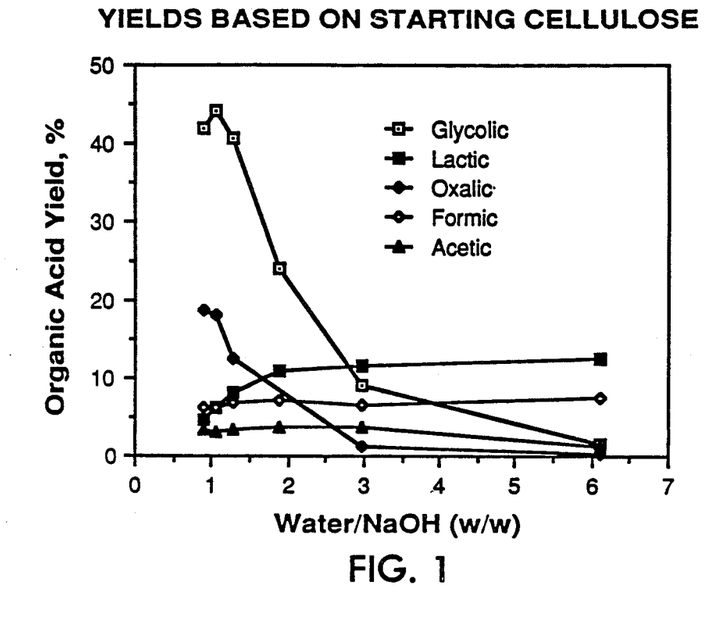
FIG. 1 shows the effect of the water/NaOH ratio on the yields of organic acids based on starting cellulose. The reaction conditions were 10 g cellulose in 250 ml alkali solution at 240° C. for 17 min.
Figure 2:
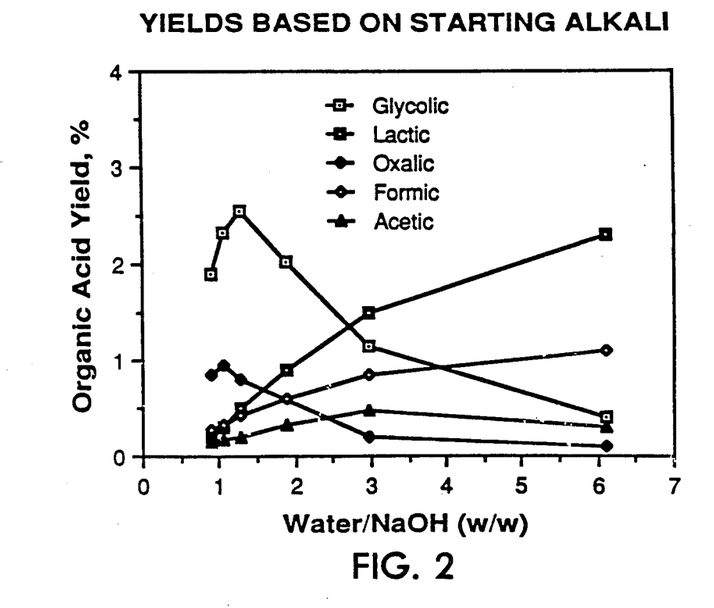
FIG. 2 shows the effect of the water/NaOH ratio on the yields of organic acids based on starting alkali. The reaction conditions were the same as for FIG. 1.

The role of the ratio of water-to-alkali on yields of organic acids is illustrated in FIGS. 1 and 2. These data were obtained by reacting 10 g of cellulose in 250 ml volumes of concentrated NaOH solutions having different water-to-alkali ratios at 240° C. for 17 min. (See Example 1 below for complete experimental details.) FIG. 1 shows the yields of organic acids based on starting cellulose. The effect of the ratio of water-to-alkali on the yields of organic acids based on starting alkali is shown in FIG. 2. As can be seen from FIGS. 1 and 2, an unexpectedly rapid rise in the yields of glycolic and oxalic acids occurs beginning at a water-to-alkali ratio of about 3 and continuing as the ratio decreases to approximately 0.8. In contrast, the yield of lactic acid decreases as the ratio of water-to-alkali decreases from 3, and the yields of formic and acetic acids stay about constant or decrease as the ratio of water-to-alkali decreases from 3 depending on whether the yields are based on starting cellulose (FIG. 1) or starting alkali (FIG. 2). The uniquely high yields of glycolic and oxalic acids at this select range of water-to-alkali ratios could not be predicted from the results of previous investigators.

In the practice of the invention, a ratio of alkali-to-polysaccharide of 1 or greater is used. The term "alkali-to-polysaccharide ratio" is used herein to describe the relative amount in parts by weight of alkali (based on NaOH) and parts by weight of polysaccharide or polysaccharide-containing material (on a moisture and ash-free basis) used.

Figure 3:
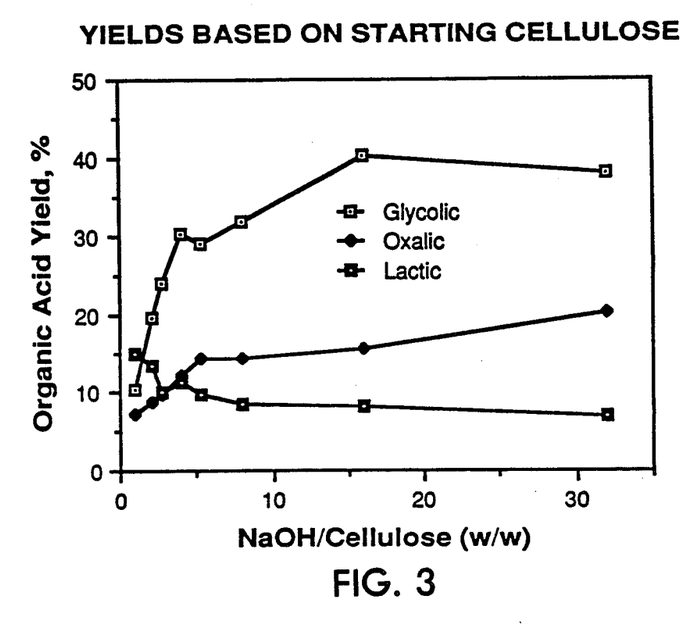
FIG. 3 shows the effect of the NaOH/cellulose ratio on the yields of organic acids based on starting cellulose. The reaction conditions were 250 ml 16N NaOH (water/NaOH = 1.28) at 240° C. for 25 min.
Figure 4:
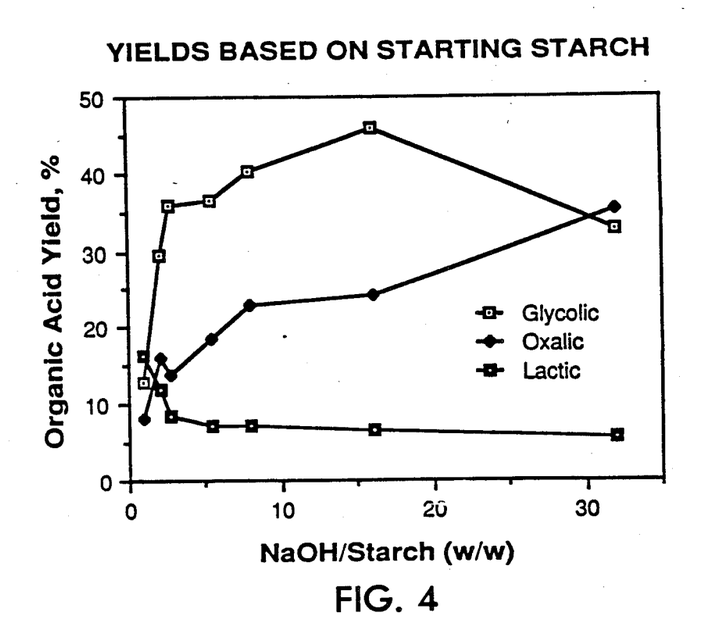
FIG. 4 shows the effect of the NaOH/starch ratio on the yields of organic acids based on starting starch. The reaction conditions were 250 ml 16N NaOH (water/NaOH =1.28) at 240° C. for 60 min.
Figure 5:
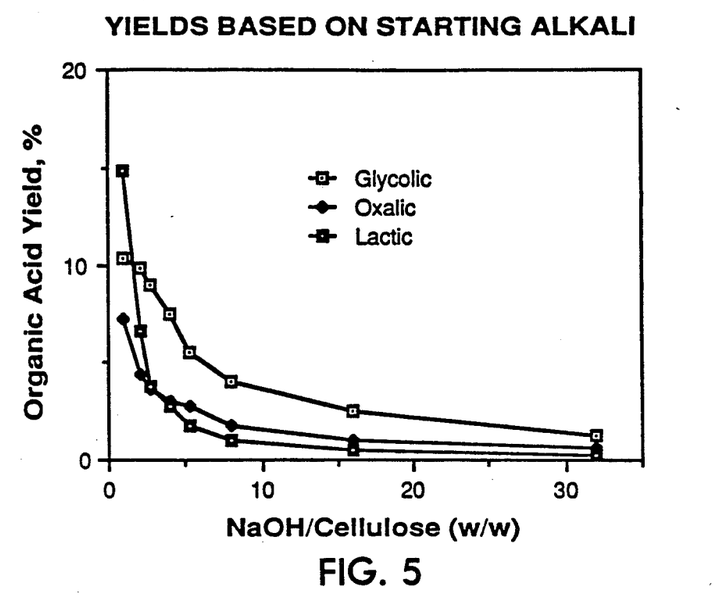
FIG. 5 shows the effect of the NaOH/cellulose ratio on the yields of organic acids based on starting alkali. The reaction conditions were the same as for FIG. 3.
Figure 6:
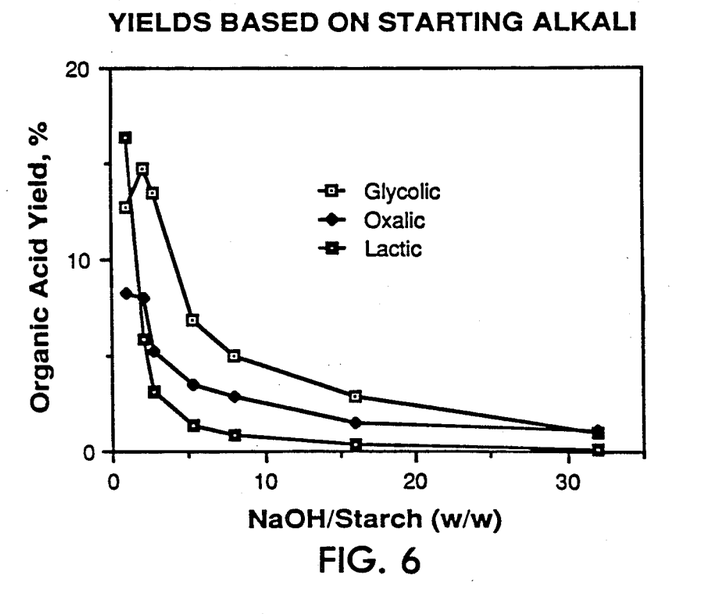
FIG. 6 shows the effect of the NaOH/starch ratio on the yields of organic acids based on starting alkali. The reaction conditions were the same as for FIG. 4.

The role of the ratio of alkali-to-polysaccharide on the yields of organic acids is illustrated in FIGS. 3–6. Varying amounts of cellulose or starch were reacted with 250 ml of 16N NaOH (water/NaOH =1.28) at 240° C. for 25 min (cellulose) or 60 min (starch). (See Example 2 below for complete experimental details.) FIGS. 3 and 4 show the effect of NaOH/cellulose and NaOH/starch ratios, respectively, on the yield of organic acids based on starting cellulose or starch. FIGS. 5 and 6 show the effect of NaOH/cellulose and NaOH/starch ratios on the yields of organic acids based on starting alkali. Generally, the yields of glycolic and oxalic acids increase as the amount of alkali relative to cellulose or starch is increased. FIGS. 3 and 4 indicate that best yields are obtained at ratios of about 2 and above. However, as shown in FIGS. 5 and 6, ratios beginning at 1 and above result in high yields based on starting alkali. Where the polysaccharide starting material is very inexpensive, e.g., cotton waste or straw, the cost of alkali becomes important, and therefore a lower ratio of alkali-to-polysaccharide is preferred for reasons of economy. The upper limit of alkali-to-polysaccharide ratio is determined more by economic considerations; the point where yields level off or decrease is generally considered the upper limit.

The method of the invention is carried out at elevated temperatures. The reaction temperature must be sufficiently high so as to promote the thermochemical degradation of the polysaccharide-containing material at a rate which is not unduely slow; conversely, the temperature must not be so high as to cause undue deterioration of the organic acid products. In general, the operative temperature range is 200° to 300° C., and preferably 220° to 280° C.

The reaction of the polysaccharide-containing material with the concentrated alkaline solution is carried for a time sufficient to thermochemically degrade the polysaccharide material into organic acids, generally, at least 4 minutes. The upper limit, with regard to reaction time, is determined more by economic considerations, and reactions are discontinued where yields level off or decrease. In general, reaction times of 4 to 30 minutes optimize product yields from cellulose, Reaction times from 10 to 60 minutes optimize product yields from starch. The roles of temperature and time at 240° and 260° C. for 3.5 to 25 minutes (cellulose) and 4 to 60 minutes (starch) are discussed in detail below in Example 3, with reference to FIGS. 7 and 8.

In contrast to the reaction mixtures of Bannister which were non-fluid, dry-like masses of cellulosic materials mixed with alkali and a very small amount of water and the reaction mixtures of Chesley et al. which were fluid slurries of cellulosic material in dilute, aqueous alkaline solutions, the reaction mixtures of the invention after the addition of the concentrated alkaline solution range from (1) non-fluid but wet masses of cellulosic or starch materials mixed with concentrated, aqueous alkaline solutions (see Examples 4, 5, and 7 below) to: (2) fluid slurries of polysaccharide materials in concentrated, aqueous alkaline solutions (see Examples 3 and 6 below). Thus, the reaction mixtures of the invention do not resemble those of either Bannister or Chesley et al.

Polysaccharide-containing materials useful for the practice of the invention include starch and starch-containing materials such as corn, wheat, rice, and the like; cellulose, hemicellulose, and materials containing cellulose or hemicellulose, such as rice straw, sawdust, corn cobs, corn stalks, wood chips, wheat straw, cotton waste, and the like.

The yields of organic acids obtained from cellulose, starch, and various polysaccharide-containing materials are shown in Table 1. The monosaccharide, glucose, and disaccharide, sucrose, were reacted for purposes of comparison. All starting materials were reacted in 16N NaOH (water/NaOH =1.28) at 240° C. at an optimum NaOH/carbohydrate material ratio, i.e., 16, found earlier for yields of glycolic acid from cellulose and starch. Reaction times selected were those found earlier to be adequate for complete conversion of cellulose (17 min) and starch (60 min) in 16N NaOH at 240° C. Thus, 17 min was used for cellulose and cellulose-containing materials, e.g., rice straw, corn cobs, and pine sawdust, and 60 min was used for starch.

Starch produced the highest yields or glycolic and oxalic acids. Cellulose produced the next highest yield of glycolic acid and a high yield of oxalic acid. High yields of glycolic and oxalic acids were also obtained from rice straw, corn cobs, and sawdust. The conversion of rice straw, corn cobs, and sawdust appears greater than that due to the cellulose content alone of these materials. For example, the cellulose content of rice straw is typically about 50% of the total moisture- and ash-free weight of the rice straw. However, the glycolic, oxalic, lactic, formic, and acetic acid yields from rice straw were, respectively, 70%, 111%, 106%, 93%, and 200% of the yields from pure cellulose. It is believed that other components of rice straw, for example, hemicellulose and lignin, are converted to organic acids.

Conversion of the sugars, glucose and sucrose, produced entirely different yield profiles of organic acids, compared to the cellulosics and starch, and such sugars are not encompassed by the method of the invention. The different organic acid yields of sugars suggests that the alkaline, thermochemical conversion of polysaccharide materials like cellulose and starch to organic acids in accordance with the method of the invention does not involve initial degradation to simple sugars, but follows an entirely different reaction pathway.

TABLE I

| Carbohydrate Material | Yields, %[a] | | | | |
|---|---|---|---|---|---|
| | Glycolic | Oxalic | Lactic | Formic | Acetic |
| Cellulose | 40.6 | 12.6 | 8.0 | 6.8 | 3.4 |
| Rice Straw | 28.3 | 14.0 | 8.5 | 6.3 | 6.8 |
| Corn Cobs | 25.1 | 8.2 | 12.4 | 7.9 | 8.6 |
| Pine Sawdust | 22.9 | 15.5 | 6.1 | 8.3 | 5.1 |
| Starch | 45.8 | 24.2 | 6.7 | ND[b] | ND |
| Gluclose[c] | 1.9 | 10.0 | 32.4 | 4.0 | 4.3 |

TABLE I-continued

| Carbohydrate Material | Yields, %[a] | | | | |
|---|---|---|---|---|---|
| | Glycolic | Oxalic | Lactic | Formic | Acetic |
| Sucrose[c] | 4.8 | 12.4 | 36.6 | 4.5 | 3.1 |

[a]Based on starting moisture- and ash-free carbohydrate material
[b]Not Determined
[c]Not in accordance with the invention; for comparison purposes Table 2 compares conversion of cellulosic materials with pure cellulose and starch at a smaller NaOH/carbohydrate material ratio (2.67). Water/NaOH ratio, reaction times and temperature were the same as described for Table 1. As can be seen from the tables, in each case the yields of glycolic and oxalic acids based on starting carbohydrate material were decreased, with starch apparently least effected. However, on reactor-volume and starting alkali bases, the yields of glycolic and oxalic acids were approximately three times greater at a NaOH/carbohydrate material ratio of 2.67 (Table 2) compared to 16 (Table 1). The reason for this is that while the reactor volume and amount of starting alkali remained the same, the amount of reacting carbohydrate increased by a factor of 6 when the NaOH/carbohydrate material ratio decreased to 2.67 from 16. Thus, as a practical matter, one factor in the choice of NaOH/carbohydrate material ratios will be the cost of starting carbohydrate material compared to the reactor cost and the cost of recovering alkali.

TABLE 2

| Carbohydrate Material | Yields, %[a] | | | | |
|---|---|---|---|---|---|
| | Glycolic | Oxalic | Lactic | Formic | Acetic |
| Cellulose | 19.0 | 7.7 | 11.0 | 6.4 | 3.3 |
| Rice Straw | 13.7 | 9.8 | 10.1 | 5.9 | 6.8 |
| Corn Cobs | 14.4 | 7.6 | 16.4 | 5.3 | 6. |
| Pine Sawdust | 14.7 | 5.2 | 8.1 | 7.2 | 4.4 |
| Starch | 35.9 | 13.9 | 8.4 | 6.6 | 2.7 |

[a]Based on starting moisture- ash-free carbohydrate material

As stated above, the method of the invention produces unexpectedly high yields of glycolic and oxalic acids, as well as good yields of lactic, formic, and acetic acids. Smaller yields (less that about 4%) of 2-hydroxybutyric, 2-hydroxyisobutyric, 2-hydroxyvaleric, and succinic acids are also obtained.

The salts of the acids described above are present in the aqueous alkaline reaction mixture. To obtain the acids, the reaction mixture is acidified, for example, by addition of acids such as sulfuric acid, hydrochloric acid, and the like to liberate the desired organic acids from their salts. The acid products may be recovered by any of the known means for separating glycolic, oxalic, lactic, formic, and acetic acids from mixtures containing these acids. If the salts of the acids are desired, such an acidification or other step to convert the salts or acids is omitted. Although this invention is applicable to the production of organic acid salts, for the sake of simplicity and clarity, it is described for the most part with reference to the production of organic acids.

One method to obtain oxalic acid is as follows: Since the sodium salt of oxalic acid is relatively insoluble, it is first removed from the reaction mixture by filtration. Next, it is treated with lime (calcium hydroxide) to convert it to insoluble calcium oxalate with recovery of NaOH. Calcium oxalate is then converted to oxalic acid by treatment with acid, for example, sulfuric acid, to produce soluble oxalic acid and insoluble calcium sulfate.

The remaining organic acid sodium salts in the reaction product can be converted to organic acids by treatment with cation exchange, sulfuric acid, or oxalic acid. If oxalic acid is used, sodium oxalate will precipitate, and it can be recovered and converted to oxalic acid for reuse as described above. The volatile organic acids remaining in the acidified solution can be recovered and separated by appropriate means known to those in the art, for example, vacuum fractional distillation. The non-volatile acids can then be extracted by a suitable solvent, converted to esters, recovered, and separated by fractional distillation, and then converted back into acids. Alternatives to fractional distillation of organic acids and esters include ion exchange chromatography, ion exclusion chromatography, and solvent extraction.

One attractive approach to recovery of soluble organic acid salts after filtration of insoluble sodium oxalate is solvent extraction of the organic acid salts from the aqueous, alkaline solution using a suitable solvent. This procedure allows separation and reuse of the NaOH in the aqueous solution with make-up NaOH for subsequent reactions. The solvent is then separated for reuse from the organic acid salts by standard procedures such as evaporation, and the organic acid salts are processed as described above.

Another recovery alternative is the separation of insoluble sodium oxalate from the reaction product by filtration, and then reuse of the aqueous alkaline solution with make-up NaOH in subsequent reactions. The concentrations of the sodium salts of the other organic acids will build up in the subsequent reactions to the point that their solubility limits will be reached, and the organic acid salts will precipitate. A steady-state situation will eventually be reached where all organic acids produced in a given reaction will precipitate, and the precipitate separation by filtration will continue to allow reuse of the alkaline solution. The organic acid salts are processed as described above.

EXAMPLES

The following examples are intended only to further illustrate the invention and are not intended to limit the scope of the invention which is defined by the claims.

Materials.

Starch used in the examples was commercial, food-grade (CPC International Inc., Englewood Cliffs, N.J.) having a moisture content of 13%.

Cellulose was purchased commercially as a highly purified, finely powdered product (Cellulay-Cellulose, United States Biochemical Corp., Cleveland, OH) and had a moisture content of 6%.

The rice straw used was milled in a hammer mill with a 0.64 cm screen; it had a moisture content of 9% and an ash content of 15%.

The corn cobs were ground to pass an 8 mesh screen (particle diameter less than 2.36 mm), and had a moisture content of 9% and an ash content of 1%.

The pine sawdust had a moisture content of 9% and an ash content of 0.2%.

Glucose was anhydrous (Baker Scientific, Phillipsburg, N.J.).

Sucrose was commercial, food-grade and had only trace moisture.

Formic acid (88%) (Fisher Scientific Co, Fair Lawn, N.J.), glacial acetic acid and oxalic acid (J. T. Baker Chemical Co., Phillipsburg, N.J.), and glycolic acid, L(+)-lactic acid (grade L-1), DL-2-hydroxybutyric acid (sodium salt), 2-hydroxyisobutyric acid, and DL-2-hydroxyvaleric acid (sodium salt) (Sigma NY) were used as standards in high-performance liquid chromatography (HPLC) and gas chromatography (GC) analyses. Glutaric acid (Mallinckrodt, Inc., St. Louis, Mo.) was used as an internal standard in the GC analyses. Boron trifluoride (14% in propanol) (Eastman Kodak Co., Rochester, NY) was used as a derivatizing agent to produce propyl esters of the organic acids for GC analyses.

Reactions.

Reactions were performed in a 1-L magnetically-stirred autoclave equipped with a cooling coil (model AFP 1005) using a Hastelloy C liner (Autoclave Engineers, Erie, Pa.). Reactions described in Examples were all performed under nitrogen. Results were not effected by reacting under air. The concentrated alkaline solution was added to the autoclave liner. Next, the polysaccharide-containing material was added, and the mixture was mixed well. The liner was then lowered into the autoclave, and the autoclave was closed. The mixture was heated to the desired temperature, allowed to react, and then cooled to room temperature. The time required to heat reactants to selected temperatures was approximately one hour. The time required to cool the reactants to below 100° C. was 20-30 minutes, and the total time required to cool to room temperature was about one hour.

High-Performance Liquid Chromatography.

Filtered product solutions were analyzed using a Waters Associate high-performance liquid chromatograph model ALC 201 equipped with a refractive index detector model R-410 (Water Associates, Milford, Mass.) to identify water-soluble products. This was accomplished by matching retention times of product compound peaks with retention times of authentic samples. A 300 mm×7.8 mm Aminex HPX-87H organic acid analysis column (Bio-Rad Laboratories, Richmond, Calif.) was used. Elution was carried out at 60° C. using 0.002N $H_2SO_4$ at a flow rate of 0.5 ml/min. Data acquisition from the chromatographic system was by a Hewlett-Packard integrating recorder model 3388A (Hewlett Packard Co., Palo Alto, Calif.).

Gas Chromatography.

To verify the compounds identified by HPLC, both standards and well-mixed product slurries were converted to their propyl esters with $BF_3$-propanol according to the method of Salwin and Bond (*Journal of the Association of Official Analytical Chemists* 52: 41–47 (1969)). The pH of standard and product solutions was adjusted to neutral before beginning the procedure, and the product solution was diluted 1:5. Analyses of the esterified compounds were performed on a Hewlett-Packard 5880A gas chromatograph equipped with a flame ionization detector and a bonded FFAP (Quadrex Corp., New Haven, Conn.) fused-silica capillary column (25 m×0.25 mm I.D., 0.25 μm film thickness). The temperature program was 100° C. to 240° C. at 5° C./min and 10 at 240° C. The injector temperature was 225° C., and the detector temperature was 300° C. Carrier flow (He) was 1.0 ml/min. Injection volume was 1 μl with a split ratio of 80:1.

Product Identification.

The HPLC chromatograms for the alkaline degradation products and the GC chromatograms for the propyl esters of the degradation products were quite similar for all the starting materials. Since GC gave much better separation of peaks then HPLC, the GC chromatograms were used to calculate the yields of most of the compounds. Formic and acetic acids were hidden under the GC solvent peak; thus, their yields were calculated from the HPLC chromatogram. With the exception of 2-hydroxyisobutyric acid, all the other products were identified with both HPLC and GC. For 2-hydroxyisobutyric acid, the HPLC peak was hidden under the lactic acid peak. HPLC chromatograms of product solutions from reactions run in the most concentrated NaOH solutions became less sharp, indicating column deterioration. Thus, formic and acetic acid yields were not determined for most of the reactions in concentrated NaOH.

EXAMPLE 1

This example describes the effect of water-to-alkali ratios on the yields of organic acids.

Two hundred and fifty ml volumes of alkaline solution having water/NaOH ratios of 0.89, 1.05, 1.29, 1.87, 2.99, and 6.12 (22, 19, 16, 12, 8, and 4N NaOH, respectively) were added to the autoclave liner. Ten g of cellulose was added in each experiment, producing NaOH/cellulose ratios of 22, 19, 16, 12, 8, and 4, respectively. Each mixture was mixed well; the liner was lowered into the autoclave, and the autoclave was closed and heated. The mixture was held at 240° C. for 17 min before cooling to room temperature. The reaction mixture was removed from the autoclave and mixed well and sampled for analysis. FIGS. 1 and 2 show the effect of variation of the water/NaOH ratio on the conversion of cellulose to the primary organic acids produced. FIG. 1 shows the yields based on starting dry cellulose; FIG. 2 shows the yields based on starting alkali. As can be seen from FIGS. 1 and 2, an unexpectedly rapid rise in the yields of glycolic and oxalic acids occurs beginning at a water-to-alkali ratio of about 3 and continuing as the ratio decreases to approximately 0.8. FIG. 1 shows that with these reaction conditions, yields of glycolic acid of about 10% or greater based on starting cellulose were obtained at ratios of 3 to 0.8; 15% or greater yields were obtained at ratios of about 2.6 to 0.8, and 25% or greater yields were obtained at ratios of 1.9 to 0.8. Based on FIG. 1, the yield of glycolic acid appears to rapidly decline after peaking at a water/NaOH ratio of 1.05, with high yields still obtained at a ratio of 0.8. FIG. 2 indicates that the yields of glycolic acid based on starting alkali rapidly increased as the amount of alkali relative to water was increased, i.e., as the ratio of water-to-alkali decreased, beginning at a water/NaOH ratio of 3.0, and peaked at a water/NaOH ratio of about 1.28. A rapid decline in yield occurred after the peak, with high yields still obtained at 0.8. As can be seen from FIGS. 1 and 2, the yields of oxalic acid generally followed the same curve as for glycolic acid except that the yields were less.

In contrast to the curves for glycolic and oxalic acids, the yield of lactic acid decreased as the ratio of water-to-alkali decreased from 3, and the yields of formic and acetic acids stayed about constant or decreased as the ratio of water-to-alakli decreased from 3, depending on whether the yields were based on starting cellulose (FIG. 1) or starting alkali (FIG. 2). Other acids were identified, including 2-hydroxybutyric, 2-hydroxyisobutyric and 2-hydroxyvaleric acids, but their yields were usually lower than that for acetic acid.

Chesley et al, found that for their process, organic acid yields based on cellulosic (wood) used varied directly with the amount of alkali used, while organic acid yields based on alkali used varied inversely with amount of alkali used. In the instant method, the yields of both glycolic and oxalic acids based on amount of cellulose used varied directly with the amount of alkali used, and the yields of these two acids based on alkali also varied directly with the amount of alkali used.

EXAMPLE 2

This example describes the effect of alkali-to-polysaccharide ratios on the yields of organic acids.

Two hundred and fifty ml volumes of alkaline solution having water/NaOH ratios of 1.28 (16N NaOH) were added to the autoclave liner. Varying amounts of cellulose (5, 10, 20, 30, 40, 60, 80, and 160 g) were added, producing NaOH/cellulose ratios of 32, 16, 8, 5.33, 4, 2.67, 2, and 1, respectively. Each mixture was mixed well, producing mixtures which ranged from thin, milky slurries (small amounts of cellulose) to non-fluid wetted masses (large amounts of cellulose). The liner was lowered into the autoclave, the autoclave closed, the mixture reacted at 240° C. for 25 min, and the mixture cooled to room temperature. The procedure was also carried using starch and heating for 60 min.

FIGS. 3 and 4 show the effect of NaOH/cellulose and NaOH/starch ratios, respectively, on the acid yields, based on starting cellulose or starch. Generally, the yields of glycolic and oxalic acids increased as the amount of NaOH relative to cellulose or starch increased. The yield of lactic acid decreased as the amount of NaOH relative to cellulose or starch increased. FIGS. 3 and 4 indicate that best yields are obtained at ratios of about 2 and above. However, as shown in FIGS. 5 and 6, ratios beginning at 1 and above result in high yields based on starting alkali. This has particular significance if the cost of alkali relative to the polysaccharide-containing material is high.

EXAMPLE 3

This example describes the effect of time and temperature on conversion of polysaccharide to organic acids.

A 250 volume of alkaline solution having a water/NaOH ratio of 1.28 (16N NaOH) was added to the autoclave liner. Ten g of cellulose was added, producing a NaOH/cellulose ratio of 16. The resulting mixture was mixed well and produced a thin, milky slurry. The liner was then lowered into the autoclave, and the autoclave was closed. The alkaline cellulose slurry was heated for varying temperatures (240° or 260° C.) and held at varying times (3.5 to 25 minutes) before cooling to room temperature. The experiment was repeated for reaction times of 8 to 60 minutes using starch instead of cellulose.

Figure 7:
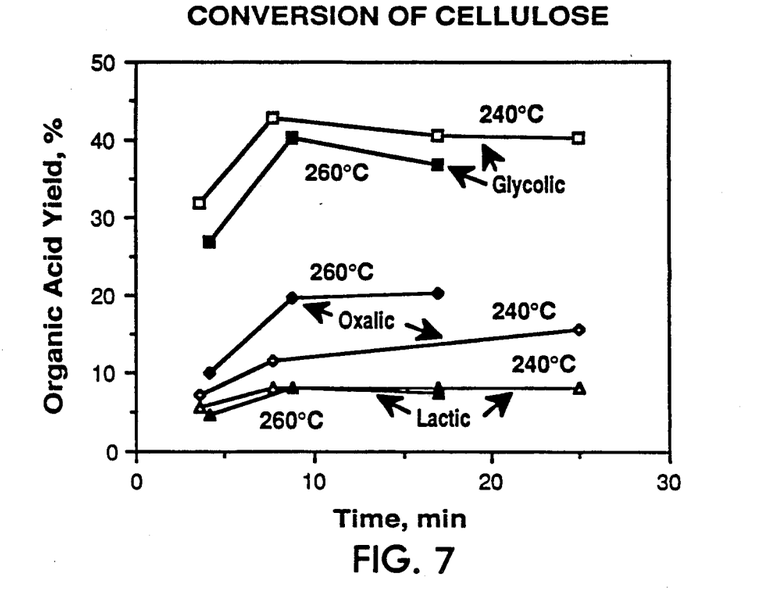
FIG. 7 shows the effect of reaction temperature and time on the conversion of cellulose to organic acids. The reaction conditions were 10 g cellulose in 250 ml 16N NaOH (water/NaOH =1.28; NaOH/cellulose =16).
Figure 8:
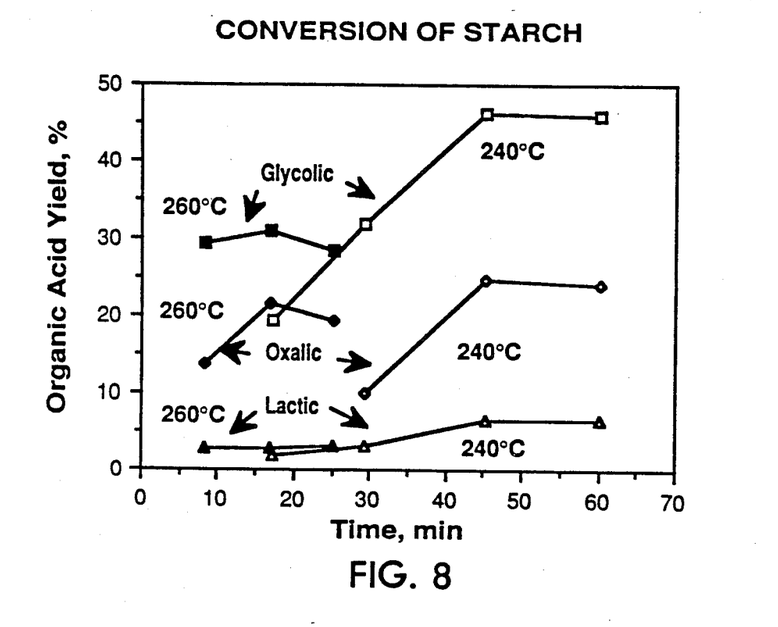
FIG. 8 shows the effect of reaction temperature and time on the conversion of starch to organic acids. The reaction conditions were 10 g starch in 250 ml 16N NaOH (water/NaOH =1.28;NaOH/starch =16).

FIGS. 7 and 8 show the effect of reaction temperature and time on the conversion of cellulose and starch with alkali solution having a water/NaOH ratio of 1.28 (16N NaOH). Maximum yields of glycolic acid were similar for cellulose and starch: 43% and 46%. respectively, at 240° C. However, the maximum glycolic acid yield from cellulose was obtained in approximately 8 min, compared to 45 min for starch. Largest oxalic acid yield of 16% from cellulose conversion at 240° C. occurred at approximately 25 min, compared to 25% oxalic acid yield at 45 min from starch. Lactic acid yield from cellulose at 240° C. peaked at 8% with a 8 min reaction time, compared to a 7% yield from starch at 45 min.

At 260° C., compared to 240° C., glycolic acid yield from cellulose dropped slightly, while oxalic acid yield increased by about one-third. At 260° C., maximum glycolic acid yield from starch dropped by one-third and occurred much earlier, compared to 240° C. Maximum oxalic acid yield also occurred earlier, but remained about the same for both temperatures.

EXAMPLE 4

A 250 volume of alkaline solution having a water/NaOH ratio of 1.28 (16N NaOH) was added to the autoclave liner. Sixty g of starch (determined on a moisture-free basis) was added, producing a NaOH/starch ratio of 2.67. The resulting mixture was mixed well to produce a wetted mass which resembled mashed potatoes. The liner was then lowered into the autoclave, and the autoclave was closed. The wetted (with alkaline solution) mass of starch was heated to a 240° C. and then held at 240° C. for one hour before cooling to room temperature. Even though the reactants were a wet mass, the product was a quite liquid slurry. This slurry was removed from the autoclave and then mixed well and sampled for analyses. The results of the analyses indicated the following yields based on starting starch: 35.9% glycolic acid, 13.9% oxalic acid, 8.4% lactic acid, 6.6% formic acid, and 2.7% acetic acid.

EXAMPLE 5

The procedure described in Example 4 was carried out, except that 60 g (moisture-free basis) of cellulose was used, resulting in a water/NaOH ratio of 1.28 and a NaOH/cellulose ratio of 2.67. The resulting mixture formed a wetted mass which had the appearance of cookie dough. After reaction at 240° C. for 17 minutes, the product was quite liquid slurry. The following yields based on starting cellulose were obtained: 19% glycolic acid, 7.7% oxalic acid, 11% lactic acid, 6.4% formic acid, and 3.3% acetic acid.

EXAMPLE 6

A 250 ml volume of alkaline solution having a water/NaOH ratio of 1.28 (16N NaOH) was added to the autoclave liner. Ten g of milled rice straw (determined on a moisture- and ash-free basis) was added, producing a NaOH/rice straw ratio of 16. The resulting mixture was a liquid slurry. After reaction at 240° C. for 17 minutes, the following yields based on moisture- and ash-free rice straw were obtained: 28.3% glycolic acid, 14% oxalic acid, 8.5% lactic acid, 6.3% formic acid, and 6.8% acetic acid.

EXAMPLE 7

The procedure described in Example 6 was carried out, except that 60 g of milled rice straw (determined on a moisture- and ash-free basis) was used, resulting in a water/NaOH ratio of 1.28 and a NaOH/rice straw ratio of 2.67. The mixture was a wetted mass of straw. After reaction at 240° C. for 17 minutes, the following yields based on moisture- and ash-free rice straw were obtained: 13.7% glycolic acid, 9.8% oxalic acid, 10.1% lactic acid, 5.9% formic acid, and 6.8% acetic acid.

It is understood that the foregoing detailed description is given merely by way of illustration and that modification and variations may be made within, without departing from the spirit and scope of the invention.

What is claimed is:

1. A method for treating a polysaccharide-containing material to produce organic acids, or salts thereof, which comprises reacting a polysaccharide-containing material with a concentrated aqueous alkaline solution at elevated temperatures in a closed system, wherein the weight ratio of water-to-alkali in said aqueous alkaline solution is 0.8/1 to 3/1, thereby yielding a product mixture comprising alkaline salts of glycolic, oxalic, lactic, formic, and acetic acids.

2. The method of claim 1 which further comprises recovering from said product mixture, acids or salts thereof, selected from the group consisting of glycolic, oxalic, lactic, formic, and acetic acids.

3. The method of claim 1 wherein said aqueous alkaline solution comprises hydroxides or carbonates of sodium or potassium.

4. The method of claim 3 wherein said aqueous alkaline solution comprises sodium hydroxide.

5. The method of claim 1 wherein the weight ratio of alkali-to-polysaccharide-containing material is 1/1 or greater.

6. The method of claim 5 wherein said weight ratio of alkali-to-polysaccharide-containing material is 2/1 or greater.

7. The method of claim 1 wherein said temperature is 200° C. to 300° C.

8. The method of claim 7 wherein said temperature is 220° C. to 280° C.

9. The method of claim 1 wherein said polysaccharide-containing material comprises starch or starch-containing material.

10. The method of claim 9 wherein said starch-containing material is selected from the group consisting of corn, wheat, and rice.

11. The method of claim 1 wherein said polysaccharide-containing material comprises cellulose or cellulose-containing material.

12. The method of claim 11 wherein said cellulose-containing material is selected from the group consisting of rice straw, sawdust, corn cobs, corn stalks, wood chips, wheat straw, and cotton waste.

* * * * *